(12) United States Patent
Mletzko et al.

(10) Patent No.: US 8,906,890 B2
(45) Date of Patent: Dec. 9, 2014

(54) VERY LOW-DOSED SOLID ORAL DOSAGE FORMS FOR HRT

(75) Inventors: Stephan Mletzko, Berlin (DE); Rolf Schurmann, Teltow (DE); Kerstin Gude, Birkenwerder (DE)

(73) Assignee: Bayer Intellectual Property GmbH, Monheim (DE)

( * ) Notice: Subject to any disclaimer, the term of this patent is extended or adjusted under 35 U.S.C. 154(b) by 190 days.

(21) Appl. No.: 13/087,701

(22) Filed: Apr. 15, 2011

(65) Prior Publication Data

US 2011/0275601 A1  Nov. 10, 2011

(30) Foreign Application Priority Data

Apr. 15, 2010 (EP) .................................... 10160072

(51) Int. Cl.
*A61K 31/56* (2006.01)
*A61K 31/57* (2006.01)
*A61K 31/565* (2006.01)
*A61K 31/585* (2006.01)

(52) U.S. Cl.
CPC ............... *A61K 31/585* (2013.01); *A61K 31/57* (2013.01); *A61K 31/565* (2013.01)
USPC ........................................................ 514/170

(58) Field of Classification Search
USPC ........................................................ 514/170
See application file for complete search history.

(56) References Cited

U.S. PATENT DOCUMENTS

| 2002/0132801 A1* | 9/2002 | Heil et al. ............... 514/175 |
| 2009/0023693 A1 | 1/2009 | Hanes et al. |

FOREIGN PATENT DOCUMENTS

| WO | WO 01/52857 A1 | 7/2001 |
| WO | WO 2005/030175 A1 | 4/2005 |
| WO | WO 2005/030176 A1 | 4/2005 |
| WO | 2005/049142 A2 | 6/2005 |
| WO | WO 2006/048261 A2 | 5/2006 |
| WO | 2006/120035 A2 | 11/2006 |
| WO | WO 2008/122439 A2 | 10/2008 |
| WO | WO 2009/112232 A2 | 9/2009 |

OTHER PUBLICATIONS

M. Notelovitz et al., "Initial 17beta-Estradiol Dose for Treating Vasomotor Symptoms", Obstetrics & Gynecology, vol. 95, No. 5, Part 1 (May 2000) pp. 726-731.
International Search Report of PCT/EP2011/055716 (Jul. 20, 2011).
William B. White, Vladimir Hanes, Vijay Chauhan and Bertram Pitt, "Effects of a New Hormone Therapy, Drospirenone and 17-β-Estradiol, in Postmenopausal Women With Hypertension," Hypertension, 48:246-253 (Jun. 26, 2006).
William B. White, Bertram Pitt, Richard A. Preston and Vladimir Hanes, "Antihypertensive Effects of Drospirenone With 17-βEstradiol, a Novel Hormone Treatment in Postmenopausal Women With Stage 1 Hypertension," Circulation, 112:1979-1984 (Sep. 27, 2005).
David F. Archer, MD, Thomas Schmelter, PHD, Matthias Schaefers, MD, PHD, Christoph Gerlinger, PHD, and Kerstin Gude, MD, PHD, "A randomized, double-blind, placebo-controlled study of the lowest effective dose of drospirenone with 17A-estradiol for moderate to severe vasomotor symptoms in postmenopausal women," Menopause: The Journal of the North American Menopause Society, 21(3):227-235 (Mar. 2014).
Gabriele Sutter, PHD, Thomas Schmelter, PHD, Kerstin Glide, MD, PHD, Matthias Schaefers, MD, PHD, Christoph Gerlinger, PHD, and David F. Archer, MD, "Population pharmacokinetic/pharmacodynamic evaluation of low-dose drospirenone with 17A-estradiol in postmenopausal women with moderate to severe vasomotor symptoms," Menopause: The Journal of the North American Menopause Society, 21(3):236-242 (Mar. 2014).

* cited by examiner

*Primary Examiner* — San-Ming Hui
(74) *Attorney, Agent, or Firm* — Thomas Blankinship

(57) ABSTRACT

The present invention relates to a very low-dosed dosage form for hormone replacement therapy (HRT). More particularly, the present invention concerns a solid oral dosage form comprising about 0.5 mg estradiol and about 0.25 mg drospirenone, and at least one pharmaceutically acceptable excipient. Despite the very low E2 and DRSP doses it has surprisingly been found that a high proportion of the women suffering from moderate to severe hot flushes actually respond to this treatment. Accordingly, the dosage form of the invention may be used as maintenance HRT or may be used already when HRT is initiated.

15 Claims, No Drawings

VERY LOW-DOSED SOLID ORAL DOSAGE FORMS FOR HRT

FIELD OF THE INVENTION

The present invention relates to a very low-dosed dosage form for hormone replacement therapy (HRT). More particularly, the present invention concerns a solid oral dosage form comprising about 0.5 mg estradiol (abbreviated "E2") and about 0.25 mg drospirenone (abbreviated "DRSP"), and at least one pharmaceutically acceptable excipient. Despite the very low E2 and DRSP doses it has surprisingly been found that a high proportion of the women suffering from moderate to severe hot flushes actually respond to this treatment. Accordingly, the dosage form of the invention may be used as maintenance HRT or may be used already when HRT is initiated.

BACKGROUND OF THE INVENTION

Estrogens, and in particular E2, have been used for decades for treating estrogen deficiency symptoms, i.e. vasomotor symptoms. Hot flushes are the most common and bothersome clinical symptom of menopause, affecting approximately 75% of postmenopausal women (Sterns et al. Lancet 2002; 360; 1851-1861). Other menopausal symptoms include mood changes, urogenital changes, sexual dysfunction, and skin changes. The increase in occurrence of hot flushes is linked with the reduction of the endogenous estrogen level that goes along with menopause. Menopausal symptoms cause discomfort and distress, ranging from tolerable to, at times, severe enough to affect a woman's quality of life. Also, the loss of endogenous estrogen during menopause accelerates the risk for chronic diseases, such as osteoporosis (Slemenda et al. Epidemiology of Osteoporisis. In: Treatment of the Postmenopausal Woman Basic and Clinical Aspects. Raven Press. New York. 1994, p. 161-168). Currently, there are more than 40 million menopausal women in the United States and almost half of them are above the age of 63 (Warren et al. Clin Obstet Gynecol 2004; 47(2);450-470). As life expectancy continues to increase, most women will spend one-third of their lifetime in postmenopause.

Although E2 doses are adjusted during therapy according to individual responses, it is, needless to say, of importance to establish the lowest E2 dose that confidentially can be used to initiate or maintain therapy.

Important factors, which are relevant in identifying the lowest initial dose of E2, include rapid and adequate release of vasomotor symptoms, and appropriateness for most women. Besides being effective, the initial dose or the maintenance dose should be well tolerated.

Notelovitz et al. (Obstet Gynecol 2000; 95(5);726-731) evaluated a range of E2 doses for symptom relief in menopausal women who needed treatment for moderate and severe vasomotor symptoms, and used the collected data to identify the ideal lowest initial dose. More particular, Notelovitz et al. conducted a randomized, double-masked, placebo-controlled 12-week study in which 333 menopausal women with moderate or severe but flushes were assigned to treatment with 0.25 mg E2, 0.5 mg E2, 1 mg E2, 2 mg E2, or placebo (administered orally). The number and severity of hot flushes were recorded on a daily basis.

Notelovitz et al. found a significant linear dose-response relationship between the E2 dose and reduction in vasomotor symptoms, assessed by the number of moderate to severe hot flushes and the hot flush weekly weighted score. At the end of the 12-week treatment period, decreases in the number of hot flushes and the hot flush weekly weighted score were significantly greater in the 0.5-, 1-, and 2-mg groups compared with the placebo group. However, at week 4 only the 1- and 2-mg groups showed significance compared to the placebo group.

Accordingly, Notelovitz et al. concluded that 1 mg E2 is the most useful starting dose for treating moderate to severe menopausal symptoms in menopausal women. According to Notelovitz et al. lower doses either require more time (0.5 mg E2) or are ineffective (0.25 mg E2) for symptom relief in women who suffer from moderate to severe vasomotor symptoms. Conversely, a higher dose of 2 mg E2 is effective for symptom relief, but is associated with increased estrogen-related adverse events.

Nevertheless, and as also emphasized by the Women's Health Initiative (WHI), there is still a need for developing and investigating dosage forms having lower doses of E2 for the treatment of vasomotor symptoms. In particular, there is a need for developing dosage forms having lower doses of E2 for the treatment of vasomotor symptoms, which have a fast and reliable onset, and hence are suitable to be used already when hormone replacement therapy is initiated, thereby avoiding initial treatment with dosage forms containing higher doses of E2.

This is also emphasised in the FDA guidelines where sponsors are encouraged to investigate dosing schedules and drug delivery systems that can achieve efficacy with the lowest possible exposures (Guidance for Industry: Estrogen and Estrogen/Progestin Drug Products to Treat Vasomotor Symptoms and Vulvar and Vaginal Atrophy Symptoms—Recommendations for Clinical Evaluation; U.S. Department of Health and Human Services; Food and Drug Administration; CDER; January 2003).

Dosage forms comprising a combination of E2 and DRSP have been described in WO 01/52857. While low-dose E2 dosage forms are formally encompassed by the disclosure in WO 01/52857, the preferred E2 dose described therein is 1 mg.

Low-dose E2-only dosage forms are described in WO 2006/048261.

An HRT product, Angeliq®, which contains 1 mg E2 and 0.5 mg DRSP, has been approved and marketed in the US.

SUMMARY OF THE INVENTION

The present inventor has now surprisingly found that an E2 dose previously believed to be too low, is effective in providing a rapid and adequate relief of moderate to severe vasomotor symptoms if such a low E2 dose is combined with a low dose of DRSP. As will be apparent from the examples provided herein, it has surprisingly been found that a high proportion of women suffering from moderate to severe hot flushes responded to treatment with a solid oral dosage form comprising a low dose of E2 (about 0.5 mg), when combined with a low dose of DRSP (about 0.25 mg).

Accordingly, such dosage forms effectively provide adequate relief of moderate to severe vasomotor symptoms, in particular moderate to severe hot flushes, in postmenopausal women already within the first few weeks of treatment. Such a low-dosed dosage form can thus be used to initiate hormone replacement therapy or, alternatively, as maintenance therapy. Furthermore, the very low-dosed dosage forms of the invention improves the bleeding behavior, in particular it lowers the frequency of breakthrough bleedings (increases the incidence rate of amenorrhea).

Accordingly, in a first aspect, the present invention relates to a solid oral dosage form comprising about 0.5 mg E2 and about 0.25 mg DRSP, and at least one pharmaceutically acceptable excipient.

In a second aspect, the present invention relates to a packaging unit consisting of a number of separately packaged and individually removable solid oral dosage forms according to the invention, and intended for oral administration for a period of at least 21 days.

In a further aspect, the present invention relates to a solid oral dosage form according to the invention for use as a medicament.

In a still further aspect, the present invention relates to a solid oral dosage form according to the invention for the prevention, treatment or alleviation of vasomotor symptoms in a woman.

In another aspect, the present invention relates to a solid oral dosage form according to the invention for lowering the frequency of breakthrough bleedings, or increasing the incidence rate of amenorrhea, in a woman.

In still another aspect, the present invention relates to a method for preventing, treating or alleviating vasomotor symptoms in a woman, said method comprising administering a solid oral dosage form according to the invention to a woman in need thereof.

In yet another aspect, the present invention relates to a method for lowering the frequency of breakthrough bleedings, or increasing the incidence rate of amenorrhea, in a woman, said method comprising administering a dosage form according to the invention to a woman in need thereof.

DETAILED DESCRIPTION OF THE INVENTION

The present invention is directed to an oral solid dosage form comprising about 0.5 mg E2 and about 0.25 mg DRSP, and at least one pharmaceutically acceptable excipient.

As indicated supra the number of patients who responded to this low-dose therapy turned out to be surprisingly high.

As it appears from the examples provided herein three patient groups were investigated; a Placebo Group, a $1^{st}$ Treatment Group receiving 0.3 mg E2 (without DRSP), and a $2^{nd}$ Treatment Group receiving 0.5 mg E2 in combination with 0.25 mg DRSP. As is abundantly clear from the data shown in the examples, the number of responders in the $2^{nd}$ Treatment Group was significantly higher than the number of responders in the $1^{st}$ Treatment Group as well as in the Placebo Group. In fact, the proportion of subjects who were responders in the $2^{nd}$ Treatment Group was as high as 62.7%.

Due to the increasing E2 (and DRSP) dose in the $2^{nd}$ Treatment Group as compared to the $1^{st}$ Treatment Group and the Placebo Group, the higher number of responders in the $2^{nd}$ Treatment Group relative to the number of responders in the $1^{st}$ Treatment Group and the Placebo Group may not appear surprising per se. What is, however, surprising is the number of responders in the $2^{nd}$ Treatment Group when compared to Angeliq© which contains a dose of E2 and DRSP that is twice as high as the E2 and DRSP doses in the dosage forms of the invention.

Since it is well-known that the numbers of responders receiving HRT with the Angeliq© preparation is high it is surprising that when the dose of E2 and DRSP is lowered by 50% (compared to the doses of E2 and DRSP in the Angeliq© preparation), the number of responders does not drop below 50%. In fact, and as already indicated above, the proportion of subjects who were responders in the $2^{nd}$ Treatment Group was as high as 62.7%.

Accordingly, a synergistic effect appears to be present between E2 in a dose of about 0.5 mg in combination with a dose of DRSP of about 0.25 mg when compared to a similar dosage form containing twice the dose of both active substances.

In addition, a common problem associated with administration of continues HRT products, such as Angeliq®, is the occurrence of breakthrough bleedings. The present inventors have found that the very low-dosed dosage forms of the invention give rise to fewer breakthrough bleedings in women, in particular postmenopausal women, as compared to HRT products containing a higher E2 dose.

When used herein the term "responder" is defined as a women who experiences a reduction (relative to baseline) of ≥2.7 moderate to severe hot flushes per day at week 4, and a reduction (relative to baseline) of ≥5.8 moderate to severe hot flushes per day at week 12.

Herein, the term "E2" (or "estradiol") is intended to mean that the E2 may be in the form of 17-α-E2 or 17-β-E2. Preferably, the E2 is in the form of 17-β-E2. The term "E2" (or "estradiol") also covers hydrated forms of E2, in particular E2 hemihydrate. It should be understood that all E2 doses mentioned herein refer to anhydrous E2. Thus, if a hydrate of E2, such as E2 hemihydrate, is employed it will be understood that a dose which is equimolar to the stated dose of anhydrous E2 should be used. By way of example, it can easily be calculated that a dose of 0.5 mg of anhydrous E2 corresponds to a dose of 0.5×1.033 mg=0.52 mg of E2 hemihydrate. The term "E2" (or "estradiol") also encompasses pharmaceutically acceptable esters of E2, such as E2 benzoate or E2 valerate, In particular E2 valerate.

The term "about 0.5 mg E2" is intended to mean that a dose slightly lower or higher than 0.5 mg may also be employed, such as an E2 dose in the range of from 0.45-0.55 mg, e.g. 0.48-0.52 mg. Specific examples of E2 doses include 0.45 mg, 0.46 mg, 0.47 mg, 0.48 mg, 0.49 mg, 0.50 mg, 0.51 mg, 0.52 mg, 0.53 mg, 0.54 mg, and 0.55 mg. The preferred E2 dose is 0.50 mg. As will be understood, similar slightly lower or higher doses of E2 hemihydrate and pharmaceutically acceptable esters of E2 may be employed.

Likewise, the term "about 0.25 mg DRSP" is intended to mean that a dose slightly lower or higher than 0.25 mg may also be employed, such as a DRSP dose in the range of from 0.20-0.30 mg, e.g. 0.23-0.27 mg. Specific examples of E2 doses include 0.20 mg, 0.21 mg, 0.22 mg, 0.23 mg, 0.24 mg, 0.25 mg, 0.26 mg, 0.27 mg, 0.28 mg, 0.29 mg, and 0.30 mg. The preferred DRSP dose is 0.25 mg.

DRSP, which is a progestin with anti-aldosterone activity, has been developed for HRT in combination with E2, and constitutes part of the commercially available HRT product, Angeliq®, cf. supra. DRSP is furthermore characterised by a pharmacological profile which is more closely related to that of endogenous progesterone than that of other synthetic progestins in use today. The main reason for incorporating DRSP in HRT products is that DRSP protects the endometrium from adverse effects of the E2.

Vasomotor symptoms comprise, but are not limited to hot flushes, sweating attacks such as night sweats, and palpitations. The vasomotor symptoms may be "mild", "moderate" or "severe" as defined by the FDA guidelines (cited supra). Thus, in the present context, the term "mild vasomotor symptoms" is defined as "sensation of heat without sweating"; the term "moderate vasomotor symptoms" is defined as "sensation of heat with sweating, but able to continue activity"; and the term "severe vasomotor symptoms" is defined as "sensation of heat with sweating, causing cessation of activity".

Psychological symptoms of estrogen deficiency comprise, but are not limited to, insomnia and other sleep conditions, poor memory, loss of confidence, mood changes, anxiety, loss of libido, difficulties in concentration, difficulty in making decisions, diminished energy and drive, irritability and crying spells. The treatment or alleviation of the aforementioned symptoms can be associated with the perimenopausal phase of a woman's life or after, sometimes long time after, menopause. It is anticipated that the dosage form of the invention is also applicable to these and other transient symptoms during the perimenopausal phase, menopause, or postmenopausal phase. Moreover, the aforementioned symptoms can be alleviated if the cause of the estrogen deficiency is hypogonadism, castration or primary ovarian failure. In another embodiment of the invention, the dosage form of the invention is used for the prevention, treatment or alleviation of permanent effects of estrogen deficiency. Permanent effects comprise physical changes such as urogenital atrophy, atrophy of the breasts, cardiovascular disease, changes in hair distribution, thickness of hair, changes in skin condition and osteoporosis. Urogenital atrophy, and conditions associated with it such as vaginal dryness, increase in vaginal pH and subsequent changes in flora, or events which lead to such atrophy, such as decreases in vascularity, fragmentation of elastic fibres, fusion of collagen fibres, or decreases in cell volume, are symptoms thought to be particularly relevant to be prevented, treated or alleviated with the dosage form of the invention. Furthermore, the dosage form of the invention is thought to be relevant to other urogenital changes associated with estrogen deficiency, decreases in mucus production, changes in cell population, decreases in glycogen production, decreases in growth of lactobacilli or increases in growth of streptococci, staphylococci, or coliform bacilli. Other associated changes that are preventable or treatable by administration of the dosage form of the invention are those that may render the vagina susceptible to injury or infection, such as exudative discharges, vaginitis, and dyspareunia.

Furthermore, infections of the urinary tract and incontinence are other common symptoms associated with lowered estrogen levels. Other embodiments of the invention include the prevention, treatment or alleviation of physical changes associated with estrogen deficiency, such as changes in the skin, changes in hair distribution, thickness of hair, atrophy of the breasts, or osteoporosis. Furthermore, bone demineralisation, reduction of bone mass and density, thinning and interruption of trabeculae, and/or consequent increase in bone fractures or bone deformations are thought to be particularly relevant. The prophylactic treatment of osteoporosis is an interesting therapeutic application of the dosage form of the invention. A particularly interesting embodiment of the invention is directed to lessening the frequency, persistence, duration and/or severity of hot flushes (in particular moderate to severe hot flushes), sweating attacks, palpitations, sleep conditions, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and osteoporosis (including prevention of osteoporosis), most notably hot flushes, sweating attacks, palpitations, sleep conditions, mood changes, nervousness, anxiety, urogenital atrophy, atrophy of the breasts, as well as prevention or management of osteoporosis. Another interesting embodiment of the invention is directed to prevention, treatment or alleviation of hot flushes, sweating attacks, palpitations, sleep conditions, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and osteoporosis (including prevention of osteoporosis), most notably hot flushes, sweating attacks, palpitations, sleep conditions, mood changes, nervousness, anxiety, urogenital atrophy, atrophy of the breasts, as well as prevention or management of osteoporosis.

As will be understood, the dosage form of the invention is suitable to be used already as the initial treatment of the above-mentioned conditions, in particular for the prevention, treatment or alleviation of moderate to severe vasomotor symptoms, such as hot flushes. Alternatively, the dosage form of the invention may be used as maintenance therapy, i.e. women suffering from vasomotor symptoms may, after initial treatment with a higher-dosed HRT product, such as Angeliq©, switch down to the HRT product described herein.

In a preferred embodiment, the woman to be treated according to the invention is a postmenopausal woman.

The terms "perimenopause", "menopause" and "postmenopause" are used in their conventional meaning, e.g. as defined in Section A of "Menopause Practice: A Clinicians's Guide", $3^{rd}$ Edition, 2007, The North American Menopause Society (NAMS). More particularly, the term "menopause" is understood as the last natural (ovary-induced) menstruation. It is a single event and a result of an age-dependent dysfunction of the ovarian follicles. Menopause results from the ovaries decreasing their production of the sex hormones estrogen and progesterone. When the number of follicles falls below a certain threshold, the ovaries can no longer produce mature follicles and sex hormones. The ability to reproduce ends with menopause. The perimenopausal phase begins with the onset of climacteric symptoms when the cycle becomes irregular and ends one year after menopause. The end of perimenopausal phase can be identified after a protracted period of time without bleeding. Postmenopause is the phase that begins at menopause and continues until death.

The woman to be treated according to the invention may be a hysterectomised or non-hysterectomised woman. In an interesting embodiment of the invention, the woman to be treated according to the invention is a non-hysterectomised woman, in particular a non-hysterectomised postmenopausal woman.

Hysterectomy is the surgical removal of the uterus. A total hysterectomy is removal of the uterus and cervix. A partial hysterectomy is removal of the uterus leaving the stump of the cervix (also called supra-cervical). Hysterectomy can be accompanied by surgical removal of the ovaries (oophorectomy). Removal of the female gonads, the ovaries, is female castration. Women who undergo total hysterectomy with bilateral salpingo-oophorectomy (removal of both ovaries, i.e. castration) lose most of their hormone production, including many estrogens and progestins. A woman who is undergoing natural menopause has intact and functional female organs, while a woman who has been hysterectomised and castrated does not. Accordingly, in the present context the term "hysterectomised woman" refers to a woman who has undergone total or partly hysterectomy, and a "non-hysterectomised woman" refers to a woman who has not undergone total or partly hysterectomy.

As discussed supra, the dosage form of the invention is suitable to be used already as the initial treatment of the above-mentioned conditions, in particular for the prevention, treatment or alleviation of moderate to severe vasomotor symptoms, such as hot flushes. Accordingly, in an interesting embodiment, the dosage form of the invention is administered to a woman who has not previously received estrogen therapy, or who is not currently receiving estrogen therapy. In another interesting embodiment of the invention, the dosage form of the invention is administered to a woman who has previously received estrogen therapy, or is currently receiving estrogen therapy, in particular estrogen therapy where the administered daily dose of E2 is >0.5 mg.

In the present context, the term "oral solid dosage form" generally refers to tablets (both swallowable-only and chewable forms), capsules, granules, granules enclosed in sachets and pills. Hence, the dosage form of the invention may be in the form of a tablet, capsule, gelcap, granule, sachet or a pill. In a preferred embodiment of the invention, the dosage form is in the form of a tablet or a capsule, in particular in the form of a tablet.

The dosage form of the invention is preferably provided in the form of an immediate release dosage form. When used herein, the term "immediate release" means that at least 70% of at least one, but preferably both, of the active ingredients are dissolved within 30 minutes when subjected to dissolution testing in 900 ml water, or 900 ml 0.1N HCl, at 37° C. using USP XXIII Paddle Method II operated at a stirring rate of 50 rpm. In a preferred embodiment, at least 80% of the at least one, but preferably both, active ingredients are dissolved within 30 minutes when subjected to dissolution testing as described above. In an even more preferred embodiment, at least 90% of the at least one, but preferably both, active ingredients are dissolved within 30 minutes when subjected to dissolution testing as described above.

Preparation of immediate release dosage forms is well-known to the skilled person. A general description of various factors influencing the dissolution properties are described in, e.g., Remington's Pharmaceutical Sciences, 18$^{th}$ Edition, 1990, Chapter 31, page 591-595. For example, immediate release dosage forms may be prepared by providing the active ingredient(s) in micronized form, such as described in WO 01/52857. Alternatively, the active ingredient(s) may be deposited on the surface of inert carrier particles, e.g. by dissolving the active ingredient(s) in a suitable organic solvent and then spraying the active ingredient(s) onto the surface of said inert carrier particles, such as described in WO 01/52857. As a further alternative, immediate release dosage forms may be prepared by incorporating dissolution-promoting excipients in the dosage form, such as described in WO 01/52857. Preferred dissolution-promoting excipients are surfactants, such as those mentioned from page 5, line 5, to page 7, line 4, of WO 2006/128907. Among these surfactants the so-called polysorbates are preferred, in particular polysorbate 80. As will be known to the skilled person, the polysorbates are commercially available under the trademark Tween®. As a still further alternative, immediate release dosage forms may be prepared by providing the active ingredient(s) in amorphous form, such as described in WO 2009/138224.

When used herein, the term "micronized" means that the active ingredient(s) has the following particle size distribution, as determined by laser diffraction: 90% of the particles have a diameter of ≤20 μm, and 50% of the particles have a diameter of ≤10 μm, preferably ≤5 μm. It should be understood that the term "micronized" also means that the particle size distribution, as determined by laser diffraction, is such that 90% of the particles have a diameter greater than 0.1 μm, preferably greater than 0.2 μm. The determination of particle size by laser diffraction may be carried out using Sympatec HELIOS, (dispersion) operated with a pressure of 1-4 bar.

As mentioned above, the dosage form of the invention preferably exhibits immediate release of the active ingredient(s). This, in turn, means that the disintegration time of the dosage form preferably is short in order to enable rapid release of the active ingredient(s). The disintegration time should preferably be less than 10 minutes, more preferably less than 5 minutes, as determined according to the United States Pharmacopoeia (USP 27; chapter <701>) without using a disc. In an even more preferred embodiment, the disintegration time is less than 4 minutes, such as less than 3 minutes, e.g. less than 2 minutes.

By the term "bioavailability" is meant the amount of DRSP or E2, that has been absorbed into the circulating blood following oral administration and is often determined relative to the amount present in the circulating blood following intravenous (i.v.) administration of a similar amount of the same active ingredient. The bioavailability may be determined as the ratio $AUC_{0-24h}$ (oral administration)/$AUC_{0-24h}$ (i.v. administration).

As described in e.g. WO 2006/048261, a dosage form containing a low dose of E2 may become chemically unstable in the presence of excipients, which have decomposing, such as oxidising, potentials greater than or similar to polyvinylpyrrolidone (PVP). Accordingly, it is preferred that the amount of such excipients is not too high in the dosage form of the invention. Therefore, an interesting embodiment of the invention encompasses a dosage form in which the weighed ratio between PVP and E2 is 10:1 or less. In absolute numbers, the dosage form of the invention preferably contains less than 5 mg PVP, such as about 4 mg PVP.

By the term "polyvinylpyrrolidone" (or "PVP") is meant a synthetic polymer having the empirical formula $(C_6H_9NO)_n$ and a molecular weight ranging from 2,500 to 3,000,000 and which consists essentially of linear 1-vinyl-2-pyrrolidone groups. Obviously, other excipients having the same oxidising power as PVP with respect to E2 is preferably to be excluded or used in limited amounts in the dosage form of the invention. An example of such other excipient may be Crospovidone. When used in an solid oral dosage form, PVP has a diversity of functions, such as acting as a disintegrant, as a dissolution aid (solubiliser, improvement of the wettability), as a suspending agent and as a tablet binder. PVP is, in particular, used in connection with highly hydrophobic drugs so as to overcome the critical step of solubilising the active drug in the gastric fluid before the actual dissolution can take place.

In order to improve the chemical stability of the active ingredient(s) present in the dosage form of the invention, but in particular E2, may be complexed with a cyclodextrin.

The term "E2-cyclodextrin complex" or "E2 complexed with cyclodextrin" is intended to mean a complex between E2 and a cyclodextrin, wherein the E2 molecule is at least partially inserted into the cavity of a cyclodextrin molecule. The molar ratio between E2 and the cyclodextrin may be adjusted to any desirable value. In interesting embodiments of the invention, a molar ratio between E2 and the cyclodextrin is from about 2:1 to 1:10, preferably from about 1:1 to 1:5, most preferably from about 1:1 to 1:3, such as 1:1 or 1:2, in particular 1:2. Furthermore, the E2 molecule may at least partially be inserted into the cavity of two or more cyclodextrin molecules, e.g. a single E2 molecule may be inserted into two cyclodextrin molecules to give 1:2 ratio between E2 and the cyclodextrin. Similarly, the complex may contain more than one E2 molecule at least partially inserted into a single cyclodextrin molecule, e.g. two E2 molecules may be at least partially inserted into a single cyclodextrin molecule to give a 2:1 ratio between E2 and cyclodextrin. Complexes between E2 and cyclodextrins may be obtained by methods known in the art, e.g. as described in U.S. Pat. No. 5,798,338 and EP 1 353 700.

The term "DRSP-cyclodextrin complex" or "DRSP complexed with cyclodextrin" is intended to mean a complex between DRSP and a cyclodextrin, wherein the DRSP molecule is at least partially inserted into the cavity of a cyclodextrin molecule. The molar ratio between DRSP and the cyclodextrin may be adjusted to any desirable value. In interesting embodiments of the invention, a molar ratio between DRSP and the cyclodextrin is from about 2:1 to 1:10, preferably from about 1:1 to 1:5, most preferably from about 1:1 to 1:3, in particular 1:3. Furthermore, the DRSP molecule may at least partially be inserted into the cavity of two or more cyclodextrin molecules, e.g. a single DRSP molecule may be inserted into two cyclodextrin molecules to give 1:2 or 1:3 ratio between DRSP and cyclodextrin. Similarly, the complex may contain more than one DRSP molecule at least partially inserted into a single cyclodextrin molecule, e.g. two DRSP molecules may be at least partially inserted into a single cyclodextrin molecule to give a 2:1 ratio between DRSP and cyclodextrin. Complexes between DRSP and cyclodextrins may be obtained by methods known in the art, e.g. as described in U.S. Pat. No. 6,610,670 and references therein.

The term "cyclodextrin" is intended to mean a cyclodextrin or a derivative thereof as well as mixtures of various cyclodextrins, mixtures of various derivatives of cyclodextrins and mixtures of various cyclodextrins and their derivatives. The cyclodextrin may be selected from the group consisting of α-cyclodextrin, β-cyclodextrin, γ-cyclodextrin and derivatives thereof. β-cyclodextrin is particularly preferred. The cyclodextrin may be modified such that some or all of the primary or secondary hydroxyl groups of the macrocycle are alkylated or acylated. Methods of modifying these hydroxyl groups are well known to the person skilled in the art and many such modified cyclodextrins are commercially available. Thus, some or all of the hydroxyl groups of the cyclodextrin may have been substituted with an O—R group or an O—C(O)—R group, wherein R is an optionally substituted $C_{1-6}$-alkyl, an optionally substituted $C_{2-6}$-alkenyl, an optionally substituted $C_{2-6}$-alkynyl, an optionally substituted aryl or heteroaryl group. Thus, R may be a methyl, an ethyl, a propyl, a butyl, a pentyl, or a hexyl group, i.e. O—C(O)—R may be an acetate. Furthermore, the hydroxyl groups may be per-benzylated, per-benzoylated, benzylated or benzoylated on just one face of the macrocycle, i.e. only 1, 2, 3, 4, 5 or 6 hydroxyl groups is/are benzylated or benzoylated. Naturally, the hydroxyl groups may also be per-alkylated or per-acylated, such as per-methylated or per-acetylated, alkylated or acylated, such as methylated or acetylated, on just one face of the macrocycle, i.e. only 1, 2, 3, 4, 5 or 6 hydroxyl groups is/are alkylated or acylated, such as methylated or acetylated. Commonly used cyclodextrins are hydroxypropyl-β-cyclodextrin, DIMEB, RAMEB and sulfoalkyl ether cyclodextrins, such as sulfobutyl ether cyclodextrin (available under the trademark Captisol®). Although cyclodextrin-complexed active ingredients are indeed contemplated, the dosage form, in one embodiment of the invention, does not contain any cyclodextrin.

In the present context, the term "$C_{1-6}$-alkyl" is intended to mean a linear or branched saturated hydrocarbon chain having from one to six carbon atoms, such as methyl; ethyl; propyl, such as n-propyl and isopropyl; butyl, such as n-butyl, isobutyl, sec-butyl and tert-butyl; pentyl, such as n-pentyl, isopentyl and neopentyl; and hexyl, such as n-hexyl and isohexyl. Likewise, the term "$C_{1-4}$-alkyl" is intended to mean a linear or branched saturated hydrocarbon chain having from one to four carbon atoms, such as methyl; ethyl; propyl, such as n-propyl and isopropyl; and butyl, such as n-butyl, isobutyl, sec-butyl and tert-butyl.

Although various cyclodextrin complexes of DRSP and E2 are described above, it is currently preferred that neither DRSP, nor E2, is complexed with a cyclodextrin. Accordingly, in a preferred embodiment, the dosage form of the invention does not contain a cyclodextrin.

The term "binder", as used herein, is generally meant to describe an agent that imparts cohesive qualities to the powdered material(s), thus linking primary particles of powdered materials to secondary aggregates. When manufacturing tablets using a process implying directly compressing a powdery mixture of the active ingredient into tablets, a binder is added to the powder mixture so as to increase the cohesion within the tablet during the compression steps. Accordingly, the binder is said to be included in the "external phase". Conversely, when manufacturing dosage forms wherein the active ingredient is combined with excipients in a granulate, i.e., wherein the manufacturing process implies a granulation step, the binder may be added to the granulation mixture so as to stabilise the resulting granules. Then, the binder is said to be present in the "internal phase". The binder may also be added after completion of the granulation step, which relate to the binder in the "external phase". Thus, it is to be understood that the term "internal phase" refers to the composition inside the granules and the term "external phase" refers to the composition outside the granules. In some interesting embodiments of the invention, the binder is preferably in the "internal phase". When wishing to have the binder in the "internal phase", the skilled artisan knows that the binder can optionally be added as a dry powder to the mixture of powdered materials. Another option is to dissolve or suspend the binder in water or any other suitable solvent or mixture of solvents including aqueous solutions, which is then used as granulation liquid. Still another option is to add the binder partly as a dry powder to the powder mixture and partly in dissolved or suspended form via the granulation liquid.

The term "first choice binder" encompasses a binder that act as a binder (in dry as well as in wetted, swelled and dissolved form) and which also has solubilising properties. PVP is the sole example of such a binder. The term "second choice binder" encompasses binders that act as a binder, in dry, wetted, swelled or dissolved form in the preparation of an oral dosage form. They are characterised by lacking or having limited wettability properties. That is to say that upon contacting an estrogen, such as E2, with a media (such as an aqueous solution) comprising a "second choice binder", the contact angle between the media and the estrogen is not effectively decreased or is not decreased at all. Furthermore, such a binder does normally not increase the dissolution rate of the active ingredient(s). Commonly used binders include acacia; alginic acid; alkali metal alginate; carbomer; dextrin; dicalcium phosphate; gelatin; glucose; guar gum; hydrogenated vegetable oil; magnesium aluminium silicate; spray-congealed mannitol; zein; starch, such as maize starch, potato starch, rice starch, tapioca starch or wheat starch; partly or fully modified or pregelatinized starch; starch derivatives, such as maltodextrin; partly or fully modified or pregelatinized starch; cellulose, such as microcrystalline cellulose; cellulose derivatives, such as carboxymethylcellulose, ethyl cellulose, hydroxypropyl cellulose, hydroxyethyl-methyl cellulose, hydroxypropylmethyl cellulose and methylcellulose; and mixtures thereof.

By "starch" is generally meant a substance having the empirical formula $(C_6H_{10}O_5)_n$ where n is 300-1000 and the molecular weight is of 50,000-160,000 and which consists of amylose and amylopectin, that are both polysaccharides based on α-glucose units. Starch is derived from plant materials, and is commonly found in the form of tiny microscopic granules (5-25 microns in diameter) comprised of stratified layers of starch molecules formed around a hilum nucleus. The starch granule may be round, oval or angular in shape, and consists of a radially oriented crystalline aggregate of two anhydrous D-glucose polymers: Amylose and amylopectin. The former is a straight chain polymer of several hundred glucose units linked by alpha-1-4-glycosidic linkages. Amylopectin is a branched polymer of several thousand glucose units with alpha-1-6-glycosidic linkages at the branched points and alpha-1-4 linkages in the linear regions. Individual branches may have between 20-30 glucose residues.

In specific embodiments of the invention the starch is selected from the starches that have a content of amylose in the range of 10% and 40% by weight. Typical examples are maize starch, potato starch, rice starch, tapioca starch and wheat starch.

In one embodiment of the invention, starch is used as a binder in a concentration of 1-5% by weight of the dosage form, preferably in the range of 2-3% by weight. The starch may be used in swelled, suspended or dissolved form in a granulation liquid or in the form of dry powder. Starch may be used in its unmodified, modified as well as partially modified form. When used herein for the purpose of granulating a powdery mixture of DRSP, E2 and at least one pharmaceutically acceptable excipient, the starch is preferably in the unmodified form. The total amount of starch may, however, be significantly higher than indicated above, e.g. in the range of 5-25% by weight of the dosage form.

The terms “modified starch” and “pregelatinized starch” are interchangeable terms and are meant to define starch that has been chemically and/or mechanically processed to rupture all or part of the granules in the presence of water and subsequently dried. Some types of pregelatinized starch may be modified to render them improved compressibility and flowability character. Typically pregelatinized starch contains 5% of free amylose, 15% of free amylopectin and 80% unmodified starch. Pregelatinized starch may be maize starch that is processed in the above-described chemical and/or mechanical manner. Other types of starch than maize starch may be pregelatinized, such as rice or potato starch.

The terms “partially modified starch” and “pregelatinized starch” are interchangeable terms and are meant to define a pregelatinized starch that is modified to a lower extent than pregelatinized starch. Pharmaceutical grades of fully pregelatinized starch use no additives and are prepared by spreading an aqueous suspension of ungelatinized starch on hot drums where gelatinization and subsequent drying takes place. Subjecting moistened starch to mechanical pressure produces partially pregelatinized starch.

The term “unmodified starch” is meant to define unprocessed starch as defined under the term “starch” above.

The term “cellulose derivatives” is meant to encompass cellulose in which a portion, or all, of the free hydroxy groups have been replaced by ether- and/or ester groups. Thus, a cellulose derivative is a cellulose ester and/or a cellulose ether. The ether or ester groups may have various carbon chain lengths such as chains with up to 10 carbon atoms, preferably up to 8, 6, 5, or 4 carbon atoms. Typical examples on cellulose derivatives are the carboxymethyl cellulose sodium, ethylcellulose, hydroxypropyl cellulose, hydroxypropyl methylcellulose, methylcellulose. Interesting binders are the low-substituted cellulose derivatives, especially hydroxypropyl methylcellulose and hydroxypropyl cellulose. The term “low-substituted” indicates that not less than 5% and not more than 16% of the hydroxyl groups have been replaced by an ether and/or ester group. The cellulose derivatives may be selected according to their resulting viscosity in a 2% aqueous solution. Typically, cellulose derivatives suitable as binders exhibit a resulting viscosity range in a 2% aqueous solution of 1-20 mPas, preferably of 2-12 mPas, most preferably of about 3-6 mPas. The cellulose derivative is typically used in a concentration of concentration of 0.5-5% by weight of the dosage form.

In an interesting embodiment of the invention, hydroxypropyl cellulose, such as low-substituted hydroxypropyl cellulose, is used in a concentration of 0.5-5% by weight of the dosage form, preferably in the range of 1-3% by weight.

In a preferred embodiment of the invention, the binder is present in the so-called “internal phase” of a granulated mixture together with the active ingredient(s) and optionally one or more additional pharmaceutically acceptable excipients. Thus, the binder may be suspended or dissolved in a suitable granulation liquid, which is then sprayed onto the powdery mixture of the active ingredient(s). Given the binder is used for the preparation of granulated matter the binder is preferably selected from unmodified starch, maltodextrin, hydroxypropyl cellulose and hydroxypropyl methylcellulose.

Thus, it should be understood that a binder, in some embodiments of the invention, is present in the internal phase only, i.e. internally and/or on the surface of the granulated form of the active ingredient(s). In other embodiments of the invention, the binder is present in the external phase, i.e. only outside the granules. In still other embodiments of the invention, the binder is present in the internal phase as well as in the external phase.

The dosage form of the invention may contain a super disintegrants. However, it is currently believed that the addition of super disintegrants is not necessary due to the favourable disintegration characteristics of the dosage form according to the invention. Specific examples of super disintegrants include sodium starch glycolate, croscarmellose and crosslinked PVP. Accordingly, in a preferred embodiment, the dosage form of the invention does not contain a super disintegrant.

The term “disintegrant” is meant to define an agent ensuring the disintegration process whereby an dosage form breaks up into fragments and particles, exposing a large surface area of the active ingredient(s) to the gastric fluid and thus allowing dissolution to occur more rapidly. Typical examples of “normal” disintegrants are agar; alginic acid; alginates; bentonit; veegum; cellulose derivatives, such as carboxymethyl cellulose sodium; gelatine; pectines; polymethacrylic acid derivatives of starch; unmodified, modified as well as partially modified starch; polymeric sugar derivatives, such as soya polysaccharides; polymeric cyclodextrin; and xylan. A disintegrant may be present in the internal or external phase. In an interesting embodiment of the invention, the disintegrant is starch, such as a mixture of unmodified starch and modified starch.

Additional examples of further excipients, which may be included in the dosage form of the invention, include fillers (sugars, such as lactose, sucrose, dextrose and dextrates; sugar alcohols, such as mannitol, sorbitol and xylitol; carbonates and phosphates of alkaline earth metals, such as calcium carbonate and calcium phosphate; celluloses, such as powdered cellulose and microcrystalline cellulose; colloidal silica; titanium dioxide; kaolin; talc), and lubricants (such as magnesium stearate).

Given that the dosage form is preferably in the form of a tablet, an additional critical parameter to be considered in order to provide rapid disintegration is the tablet hardness. The compressed tablet may exhibit sufficient hardness so as to resist physical stress during packaging, transport and application. On the other hand, the hardness should allow for rapid disintegration of the tablet. Thus, in one embodiment of the invention, a hardening agent is added.

In the present context, the term "hardening agent" means an excipient that is incorporated into a compressed tablet composition to impart increased hardness thereto. Exemplary hardening agents include calcium carbonate; di- and tri-calcium phosphate; calcium sulfate; microcrystalline cellulose; powdered cellulose; dextrates; dextrin; sugars, such as dextrose, fructose, lactose, mannitol, sorbitol and sucrose; glyceryl palmitostearate; kaolin; magnesium carbonate; magnesium oxide; maltodextrin; potassium chloride, sodium chloride; starch; pregelatinized starch; talc and hydrogenated vegetable oil. In a preferred embodiment, the hardening agent is modified starch.

"Hardness" of a tablet is measured as the force in N (Newton) required to break a tablet. In an interesting embodiment, the tablet of the invention has a hardness in the range of from 25 N to 120 N, preferably in the range of from 35 N to 90 N, most preferably in the range of from 40 N to 80 N, corresponding to a round-shaped tablet core of about 80 mg in weight. It is well known within the skilled artisan to define suitable hardness ranges depending on the size and the shape of the tablets.

In a preferred embodiment, the tablet core is provided with a film-coat for the ease of swallowing the tablet. The film-coating may contain film-coating agents such as hydroxypropylmethyl cellulose, macrogol, talc, and colouring agents such as titanium dioxide, ferric oxide pigment yellow.

Since the dosage form is preferably provided as an immediate release dosage form, it is preferred that the dosage form does not contain a gastric resistant film coat (enteric film coat).

The phrase "granulated form" indicates that the resulting physical form, when a powdery mixture of an active ingredient(s) and one or more excipients is transformed into partly agglomerated particles and/or granules, has a particle size larger than the unprocessed powdery mixture. The transformation may take place using any suitable apparatus known to the skilled person, preferably by contacting the powdery mixture with a granulation liquid using suitable granulation equipment, such as fluidised bed granulation.

By the term "granulating" is understood a mechanical process whereby a powder comprising the active component and excipients are partly agglomerated into particles and/or granules having a larger particle size than the unprocessed powder. In one embodiment, the powdery mixture of DRSP and E2 and excipients is contacted with a granulation liquid, which may comprise the binder, swelled, partly dissolved or completely dissolved in the granulation liquid. The granulation liquid may be any suitable solvent, but generally aqueous solutions or just water are applicable. In one embodiment, the powdery mixture is contacted with the granulation liquid using suitable equipment for wet-granulation, such as fluidised bed equipment. Furthermore, high shear granulation can be used instead of fluidised bed granulation.

In another suitable embodiment of the invention, the granulation liquid does not contain the binder. The binder is then added in dry form to the powdery mixture of the DRSP and the E2 concurrently with a granulation liquid.

As indicated supra, another aspect of the present invention is directed to a packaging unit consisting of a number of separately packaged and individually removable solid oral dosage forms as according to the invention, and intended for oral administration for a period of at least 21 days. Such a packaging unit may be prepared in a manner analogous to that of making oral contraceptives, and may, for example, be a conventional blister pack or any other form known for this purpose, such as a pack containing the appropriate number of dosage units in a sealed blister pack with a cardboard, paperboard, foil plastic backing and enclosed in a suitable cover. Each blister pack may be numbered or otherwise marked. In a preferred embodiment of the invention the oral administration is intended for 28 days, i.e. the blister pack in this case contains 28 separately packaged and individually removable dosage forms. Evidently, the number of dosage forms in this case is 28 or a multiple of 28, such as a 2 to 12 multiple 28, e.g. a 2 to 6 multiple of 28.

The invention is further illustrated by the following non-limiting examples.

EXAMPLES

Example 1

Clinical Study

Study Design

The clinical study was a multicenter, double-blind, randomized, placebo-controlled study to determine the lowest effective dose of orally administered E2 for the relief of moderate to severe vasomotor symptoms in postmenopausal women over a treatment period of 12 weeks.

The Placebo Group received daily a tablet containing 0 mg E2 (and no DRSP) for 12 weeks.

The $1^{st}$ Treatment Group received daily a tablet containing 0.3 mg E2 (and no DRSP) for 12 weeks.

The $2^{nd}$ Treatment Group received daily a tablet containing 0.5 mg E2 and 0.25 mg DRSP for 12 weeks.

All three groups had comparable mean and median values at baseline with respect to the frequency of moderate to severe hot flushes.

Efficacy

The below table shows the proportion of responders by treatment group:

| Parameter | Placebo Group | $1^{st}$ Treatment Group (0.3 mg E2) | $2^{nd}$ Treatment Group (0.5 mg E2/0.25 mg DRSP) |
|---|---|---|---|
| Number of subjects | 176 (100%) | 170 (100%) | 177 (100%) |
| Responder: | | | |
| No | 129 (73.3%) | 91 (50.8%) | 66 (37.3%) |
| Yes | 47 (26.7%) | 88 (49.2%) | 111 (62.7%) |
| p-value[1)] | | <0.0001 | <0.0001 |

[1)]p-values were determined by Fisher's exact test comparing the Treatment Group in question with the Placebo Group Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 10160072.4, filed Apr. 15, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A solid oral dosage form comprising about 0.5 mg estradiol and about 0.25 mg drospirenone, and at least one pharmaceutically acceptable excipient.

2. The dosage form according to claim 1, wherein said dosage form is a tablet.

3. The dosage form according to claim 1, wherein said estradiol is in the form of estradiol hemihydrate.

4. The dosage form according to claim 1, wherein said estradiol is in the form of a pharmaceutically acceptable ester of estradiol.

5. A packaging unit consisting of a number of separately packaged and individually removable solid oral dosage forms as defined in claim 1, and intended for oral administration for a period of at least 21 days.

6. The packaging unit according to claim 5, wherein said oral administration is for a period of 28 days.

7. The packaging unit according to claim 5, wherein the number of dosage forms is 28 or a multiple of 28.

8. The packaging unit according to claim 7, wherein the number of dosage forms is a 2 to 12 multiple of 28.

9. The packaging unit according to claim 4, wherein said packaging unit is a blister pack.

10. The dosage form according to claim 1 for use as a medicament.

11. The dosage form according to claim 1 for the prevention, treatment or alleviation of vasomotor symptoms in a woman.

12. The dosage form according to claim 11, wherein said vasomotor symptoms are moderate to severe vasomotor symptoms.

13. The dosage form according to claim 11, wherein said vasomotor symptoms are hot flushes.

14. The dosage form according to claim 1 for lowering the frequency of breakthrough bleedings, or increasing the incidence rate of amenorrhea, in a woman.

15. The dosage form according to claim 11, wherein said woman is a postmenopausal woman.

* * * * *